United States Patent
Zhang et al.

(10) Patent No.: US 11,439,465 B2
(45) Date of Patent: Sep. 13, 2022

(54) SURGICAL LASER SYSTEMS AND LASER LITHOTRIPSY TECHNIQUES

(71) Applicant: Boston Scientific Scimed, Inc., Maple Grove, MN (US)

(72) Inventors: Jian James Zhang, Santa Clara, CA (US); Rongwei Jason Xuan, Fremont, CA (US); Danop Rajabhandharaks, Santa Clara, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 238 days.

(21) Appl. No.: 16/265,226

(22) Filed: Feb. 1, 2019

(65) Prior Publication Data

US 2019/0159839 A1    May 30, 2019

Related U.S. Application Data

(63) Continuation of application No. 14/863,647, filed on Sep. 24, 2015, now abandoned, which is a continuation of application No. PCT/US2015/051687, filed on Sep. 23, 2015.

(60) Provisional application No. 62/054,582, filed on Sep. 24, 2014.

(51) Int. Cl.
*A61B 18/26* (2006.01)
*A61B 18/22* (2006.01)

(52) U.S. Cl.
CPC .............. *A61B 18/26* (2013.01); *A61B 18/22* (2013.01); *A61B 2018/2266* (2013.01); *A61B 2018/2288* (2013.01); *A61B 2018/263* (2013.01)

(58) Field of Classification Search
None
See application file for complete search history.

(56) References Cited

U.S. PATENT DOCUMENTS

| 3,467,098 | A |   | 9/1969 | Ayres |             |
|-----------|---|---|--------|-------|-------------|
| 4,204,743 | A | * | 5/1980 | Etaix | G02B 6/4204 |
|           |   |   |        |       | 385/88      |

(Continued)

FOREIGN PATENT DOCUMENTS

| DE | 37 27 003 A1    |   | 2/1988 |            |
|----|-----------------|---|--------|------------|
| DE | 38 36 337 A1    |   | 4/1990 |            |
| EP | 01292833 A2     |   | 9/1986 |            |
| JP | S61 193653 A    |   | 8/1986 |            |
| WO | WO-9105332 A1   | * | 4/1991 | A61B 18/26 |
| WO | WO 9105332 A1   |   | 4/1991 |            |

OTHER PUBLICATIONS

Merriam-Webster Dictionary, Definition of "attached", retrievedfromwww.merriam-webster.com/dictionary/attached, Dec. 14, 2021 (Year: 2021).*

(Continued)

*Primary Examiner* — Carl H Layno
*Assistant Examiner* — Manolis Pahakis
(74) *Attorney, Agent, or Firm* — Bookoff McAndrews, PLLC

(57) ABSTRACT

A laser fiber for use in performing a medical laser treatment includes an optical fiber and a fiber tip. The optical fiber includes a terminating end surface at a distal end. The fiber tip is positioned at the distal end of the optical fiber and includes a transmissive portion and a spacer portion. Laser energy discharged from the terminating end surface of the optical fiber is transmitted through the transmissive portion. The spacer portion defines a distal terminating end of the fiber tip that is spaced a predetermined distance from the terminating end surface of the optical fiber. The predetermined distance is set for shock wave generation for calculus destruction at the distal terminating end of the fiber tip.

20 Claims, 5 Drawing Sheets

(56) References Cited

U.S. PATENT DOCUMENTS

| | | | |
|---|---|---|---|
| 4,273,109 A * | 6/1981 | Enderby | A61B 18/24 219/121.75 |
| 4,695,697 A * | 9/1987 | Kosa | A61B 18/20 385/94 |
| 4,707,073 A * | 11/1987 | Kocher | B23K 26/06 219/121.6 |
| 4,718,417 A | 1/1988 | Kittrell et al. | |
| 4,732,449 A * | 3/1988 | Fan | G02B 6/2817 385/33 |
| 4,817,601 A * | 4/1989 | Roth | A61B 18/245 606/7 |
| 4,838,246 A * | 6/1989 | Hahn | A61B 1/00091 600/108 |
| 4,865,029 A | 9/1989 | Pankratov et al. | |
| 4,867,136 A * | 9/1989 | Suzuki | A61B 1/0008 600/109 |
| 4,932,954 A | 6/1990 | Wondrazek et al. | |
| 5,019,040 A * | 5/1991 | Itaoka | A61B 1/0058 604/20 |
| 5,041,121 A | 8/1991 | Wondrazek et al. | |
| 5,093,877 A * | 3/1992 | Aita | A61B 18/245 385/33 |
| 5,112,328 A | 5/1992 | Taboada et al. | |
| 5,167,686 A * | 12/1992 | Wong | G02B 6/4296 606/7 |
| 5,224,942 A | 7/1993 | Beuchat et al. | |
| 5,257,989 A | 11/1993 | Celaya et al. | |
| 5,291,570 A | 3/1994 | Filgas et al. | |
| 5,304,171 A * | 4/1994 | Gregory | A61N 5/0601 606/15 |
| 5,324,282 A | 6/1994 | Dodick | |
| 5,425,735 A | 6/1995 | Rosen et al. | |
| 5,496,309 A * | 3/1996 | Saadat | G02B 6/4204 385/88 |
| 5,526,455 A * | 6/1996 | Akita | G02B 6/4204 385/33 |
| 5,553,629 A | 9/1996 | Keipert et al. | |
| 5,568,503 A * | 10/1996 | Omori | A61B 18/22 372/70 |
| 5,594,821 A * | 1/1997 | Cheng | G02B 6/2937 385/14 |
| 5,599,341 A | 2/1997 | Mathis et al. | |
| 5,680,237 A * | 10/1997 | Cheng | G02B 6/2937 385/34 |
| 5,738,676 A * | 4/1998 | Hammer | A61F 9/008 606/17 |
| 5,738,677 A * | 4/1998 | Colvard | G02B 6/4296 606/4 |
| 5,760,362 A * | 6/1998 | Eloy | A61B 18/26 219/121.6 |
| 5,815,623 A * | 9/1998 | Gilliland | G02B 6/4244 385/88 |
| 5,840,075 A | 11/1998 | Mueller et al. | |
| 5,944,687 A | 8/1999 | Benett et al. | |
| 6,066,128 A * | 5/2000 | Bahmanyar | A61B 3/135 606/16 |
| 6,142,630 A * | 11/2000 | Koester | A61B 3/125 351/219 |
| 6,157,485 A * | 12/2000 | Cheng | G02B 6/2746 359/489.11 |
| 6,175,673 B1 * | 1/2001 | Duck | G02B 6/2817 305/33 |
| 6,203,537 B1 | 3/2001 | Adrian | |
| 6,219,481 B1 * | 4/2001 | Cheng | G02B 6/2937 385/24 |
| 6,393,179 B1 * | 5/2002 | Cheng | G02B 6/2746 385/34 |
| 6,484,052 B1 | 11/2002 | Visuri et al. | |
| 7,751,661 B2 * | 7/2010 | Kadomi | G02B 6/262 385/36 |
| 7,758,621 B2 | 7/2010 | Altshuler et al. | |
| 8,109,676 B2 * | 2/2012 | Zhovnirovsky | G02B 6/32 385/94 |
| 8,571,364 B2 | 10/2013 | Smith et al. | |
| 8,711,336 B1 * | 4/2014 | Frogget | G01S 7/4812 356/27 |
| 8,967,885 B2 * | 3/2015 | Bhagavatula | G02B 6/2552 385/93 |
| 9,429,717 B2 * | 8/2016 | Nakama | G02B 6/4214 |
| 10,560,612 B2 * | 2/2020 | Haraguchi | G02B 23/243 |
| 2002/0110321 A1 * | 8/2002 | Ouali | G02B 6/245 385/33 |
| 2002/0159693 A1 * | 10/2002 | Wolak | G02B 6/4207 385/33 |
| 2002/0181891 A1 * | 12/2002 | Alcock | G02B 6/32 385/79 |
| 2002/0186742 A1 * | 12/2002 | Flint | H01S 3/08 372/70 |
| 2003/0050534 A1 * | 3/2003 | Kazakevich | A61B 1/0607 600/178 |
| 2003/0083552 A1 * | 5/2003 | Remijan | G02B 23/2476 600/182 |
| 2003/0139041 A1 | 7/2003 | LeClair | |
| 2004/0004055 A1 | 1/2004 | Barros | |
| 2004/0012965 A1 * | 1/2004 | Yoneda | G02B 6/4296 362/294 |
| 2004/0052475 A1 * | 3/2004 | Deng | G02B 6/322 385/33 |
| 2004/0097791 A1 * | 5/2004 | Tokuda | A61B 1/00188 600/173 |
| 2004/0242963 A1 * | 12/2004 | Matsumoto | G02B 23/2469 600/127 |
| 2005/0168987 A1 * | 8/2005 | Tamaoki | F21K 9/61 362/244 |
| 2005/0283048 A1 * | 12/2005 | Gill | A61B 1/0638 600/121 |
| 2006/0200113 A1 | 9/2006 | Haffner et al. | |
| 2007/0165981 A1 * | 7/2007 | Tanaka | A61B 1/00142 600/109 |
| 2007/0195548 A1 * | 8/2007 | Wang | A61N 5/062 362/555 |
| 2008/0064925 A1 * | 3/2008 | Gill | A61B 1/00142 600/109 |
| 2008/0108867 A1 * | 5/2008 | Zhou | A61B 8/12 606/7 |
| 2009/0281385 A1 * | 11/2009 | Hatoma | A61B 1/07 600/114 |
| 2009/0287198 A1 | 11/2009 | Hanley et al. | |
| 2010/0152540 A1 * | 6/2010 | Tanoue | G02B 23/2469 600/175 |
| 2013/0114926 A1 * | 5/2013 | Moriya | G02B 6/262 385/33 |
| 2013/0223787 A1 * | 8/2013 | Bhagavatula | G02B 6/262 385/12 |
| 2013/0274726 A1 | 10/2013 | Takayama et al. | |
| 2013/0322821 A1 * | 12/2013 | Grinderslev | G02B 6/3853 385/33 |
| 2014/0288369 A1 * | 9/2014 | Henley | A61B 1/05 600/109 |
| 2016/0184022 A1 | 6/2016 | Grace et al. | |
| 2016/0213239 A1 * | 7/2016 | Fujii | A61B 1/0019 |
| 2016/0320569 A1 * | 11/2016 | Fortusini | G02B 6/3818 |
| 2017/0010456 A1 * | 1/2017 | Gopinath | G02B 6/06 |
| 2017/0059848 A1 * | 3/2017 | Haraguchi | A61B 1/00096 |
| 2020/0305703 A1 * | 10/2020 | Bala | A61B 1/00181 |

OTHER PUBLICATIONS

International Search Report and Written Opinion for PCT/US2015/051687, dated Dec. 23, 2015 (13 pages).

* cited by examiner

PHOTOS OF LASER LITHOTRIPSY OPERATIONS
USING A HO:YAG LASER AND A TM:YAG LASER

SURGICAL LASER SYSTEMS AND LASER LITHOTRIPSY TECHNIQUES

CROSS REFERENCE TO RELATED APPLICATIONS

This application is a continuation of U.S. patent application Ser. No. 14/863,647, filed Sep. 24, 2015, which is a continuation of International Application No. PCT/US2015/051687, filed Sep. 23, 2015, which is based on and claims the benefit of priority of U.S. Provisional Patent Application No. 62/054,582, filed Sep. 24, 2014. The contents of each of the above-identified applications are hereby incorporated by reference in their entirety.

BACKGROUND

Embodiments of the present invention generally relate to laser fibers for performing a medical laser treatment.

Medical lasers have been used in various practice areas, such as, for example, urology, neurology, otorhinolaryngology, general anesthetic ophthalmology, dentistry, gastroenterology, cardiology, gynecology, and thoracic and orthopedic procedures. Generally, these procedures require precisely controlled delivery of laser energy as part of the treatment protocol.

The treatment of kidney or bladder calculi or stones, Lithotripsy, is currently achieved through either ESWL (extracorporeal shock wave lithotripsy), surgery, or use of a laser (laser lithotripsy). In the laser application, a holmium doped yttrium aluminium garnet (Ho:YAG) laser rod, or a thulium doped yttrium aluminium garnet (Tm:YAG) laser rod, are used to produce laser energy having a wavelength of around 2000-2100 nm to break up stones of all types. The laser energy is typically in the form of a train of laser pulses, each having long pulse widths, such as approximately a few hundred microseconds. It is believed that a thermo-mechanical mechanism of action is in play for breaking up the stones, namely the laser energy superheats fluid in the vicinity of the stone, and creates a vaporization bubble. The vaporization bubble then expands as a shockwave and destabilizes the stone, causing it to fragment.

There is a continuous demand for improvements to laser lithotripsy and other laser procedures, such as improved laser fibers for delivering laser energy to the targeted stone or tissue.

SUMMARY

Embodiments of the present invention generally relate to a laser fiber for use in performing a medical laser treatment, such as laser lithotripsy, surgical laser systems utilizing such laser fibers, and methods of performing laser lithotripsy procedures using the laser fibers. In some embodiments, the laser fiber includes an optical fiber and a fiber tip. The optical fiber includes a terminating end surface at a distal end. The fiber tip is positioned at the distal end of the optical fiber and includes a transmissive portion and a spacer portion. Laser energy discharged from the terminating end surface of the optical fiber is transmitted through the transmissive portion. The spacer portion defines a distal terminating end of the fiber tip that is spaced a predetermined distance from the terminating end surface of the optical fiber. The predetermined distance is set for shock wave generation for calculus destruction at the distal terminating end of the fiber tip.

Embodiments of the surgical laser system include a laser generator and the optical fiber formed in accordance with one or more embodiments. The laser generator is configured to output laser energy that is optically coupled to a proximal end of the optical fiber. The laser energy is transmitted through the optical fiber and is discharged through the terminating end surface of the optical fiber and the fiber tip.

In some embodiments of a method of fragmenting a calculus, the calculus is engaged with the terminating end of the fiber tip to position the terminating end surface of the optical fiber at the predetermined distance from the calculus. Laser energy is transmitted through the optical fiber. The laser energy is discharged through the terminating end surface of the optical fiber and the calculus is exposed to the laser energy while the calculus is maintained at the predetermined distance from the terminating end surface using the spacer portion. The calculus is fragmented in response to the exposure to the laser energy.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Figure 1:
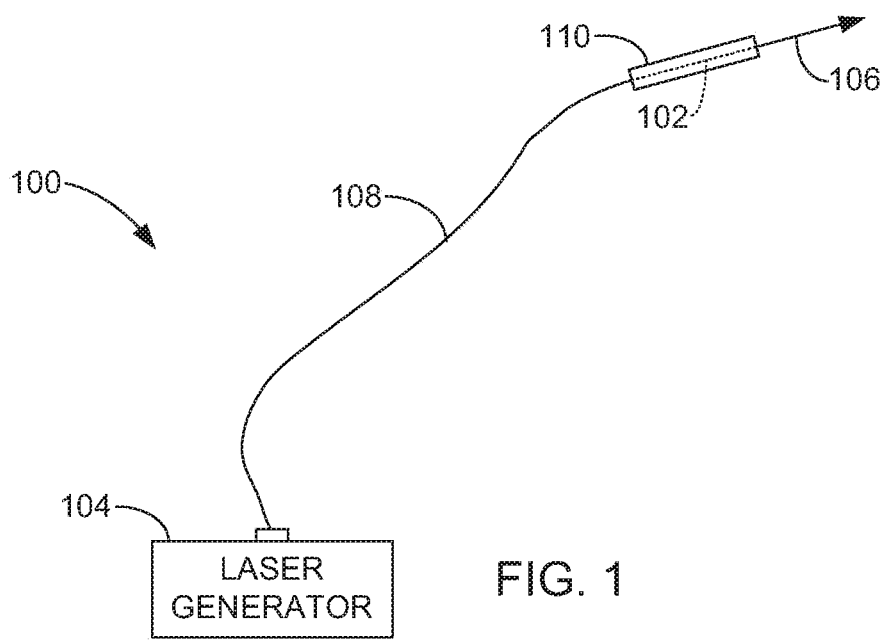
FIG. 1 is a schematic diagram of an exemplary surgical laser system in accordance with embodiments of the invention.

Embodiments of the present invention generally relate to laser fibers for use in performing a medical laser treatment, such as laser lithotripsy, surgical laser systems utilizing such laser fibers, and methods of performing laser lithotripsy procedures using the laser fibers. Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a schematic diagram of an exemplary surgical laser system 100, which includes a laser fiber 102 in accordance with one or more embodiments of the invention. FIGS. 2-7 are simplified cross-sectional views of exemplary laser fibers 102 in accordance with embodiments of the invention. FIG. 4 is a simplified cross-sectional view of a fiber tip of FIG. 4 taken generally along line 4-4.

In some embodiments, the system 100 comprises a laser generator 104 that generates laser energy 106 and a waveguide 108 optically coupling the laser generator 104 to the laser fiber 102. The laser fiber 102 either includes the waveguide 108 or is optically coupled to the waveguide 108. The laser energy 106 is discharged from a distal end of the laser fiber 102, i.e., the end of the laser fiber 102 that is adjacent to the treatment site of a patient, and can be used to perform a desired medical laser procedure, such as tissue ablation, or urinary or kidney stone fragmentation. In some embodiments, the system 100 includes a probe 110 (FIG. 1), in which at least a distal end of the laser fiber 102 is supported.

In some embodiments, the laser generator 104 comprises one or more conventional laser sources, such as laser resonators, that produce the laser energy 106 having desired properties. In some embodiments, the system 100 produces the laser energy 106 in the form of a pulse train or continuous wave. In some embodiments, the laser generator 102 includes Q-switched laser rods to produce the laser energy 106, such as, for example, a holmium doped yttrium aluminium garnet (Ho:YAG) laser rod, a thulium doped yttrium aluminium garnet (Tm:YAG) laser rod, or other conventional laser rod suitable for producing the desired laser energy 106. In some embodiments the laser energy 106 has a power of approximately 1-50 W, a pulse repetition frequency of 1-2000 Hz. and an energy level of 1 mJ-5 J. Laser energy 106 having other parameters may also be used.

Figure 2:
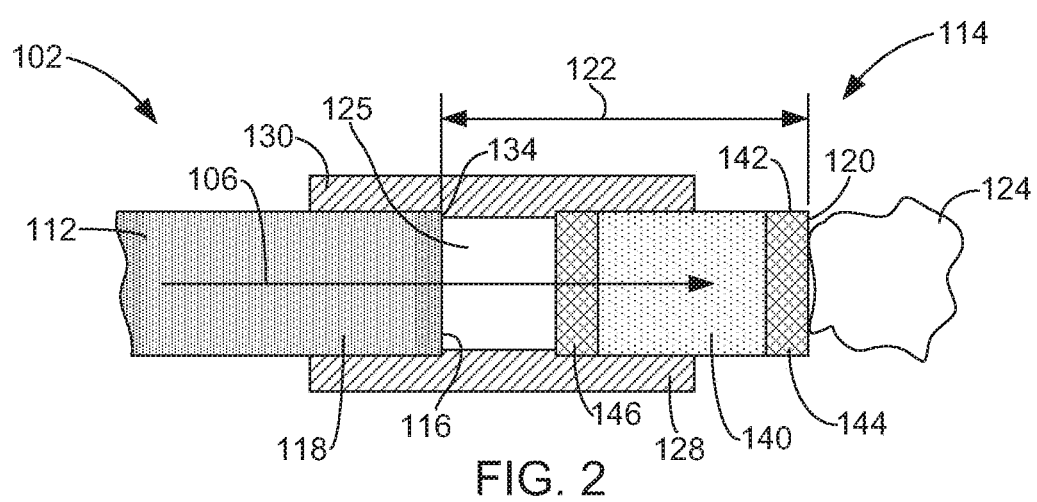
FIGS. 2 and 3 are simplified side cross-sectional views of a distal end of exemplary laser fibers in accordance with embodiments of the invention.

In some embodiments, the laser fiber 102 includes an optical fiber 112 and a fiber tip 114. The optical fiber 112 includes a terminating end surface 116 at a distal end 118. In some embodiments, the fiber tip 114 includes a distal terminating end 120 that is spaced a predetermined distance 122 from the terminating end surface 116 of the optical fiber 112. In some embodiments, the fiber tip 114 operates to protect the distal end 118 of the optical fiber. For instance, the fiber tip 114 can prevent or reduce damage to the distal end 118 of the optical fiber 112 that can occur during medical laser treatments due to contact between the distal end 118 of the optical fiber 112 and the targeted object for the laser energy 106, such as a calculus (i.e., kidney or bladder stone) 124 or tissue. In some embodiments, the fiber tip 114 forms a sealed cavity 125 around the terminating end surface 116 of the optical fiber, as shown in FIG. 2.

Figure 8:
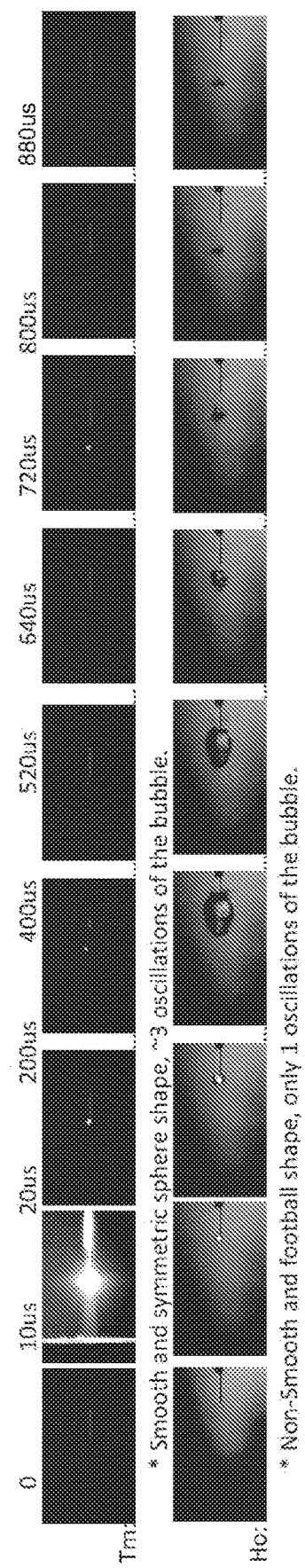
FIG. 8 shows photos of laser lithotripsy operations using exemplary lasers.
Figure 9:
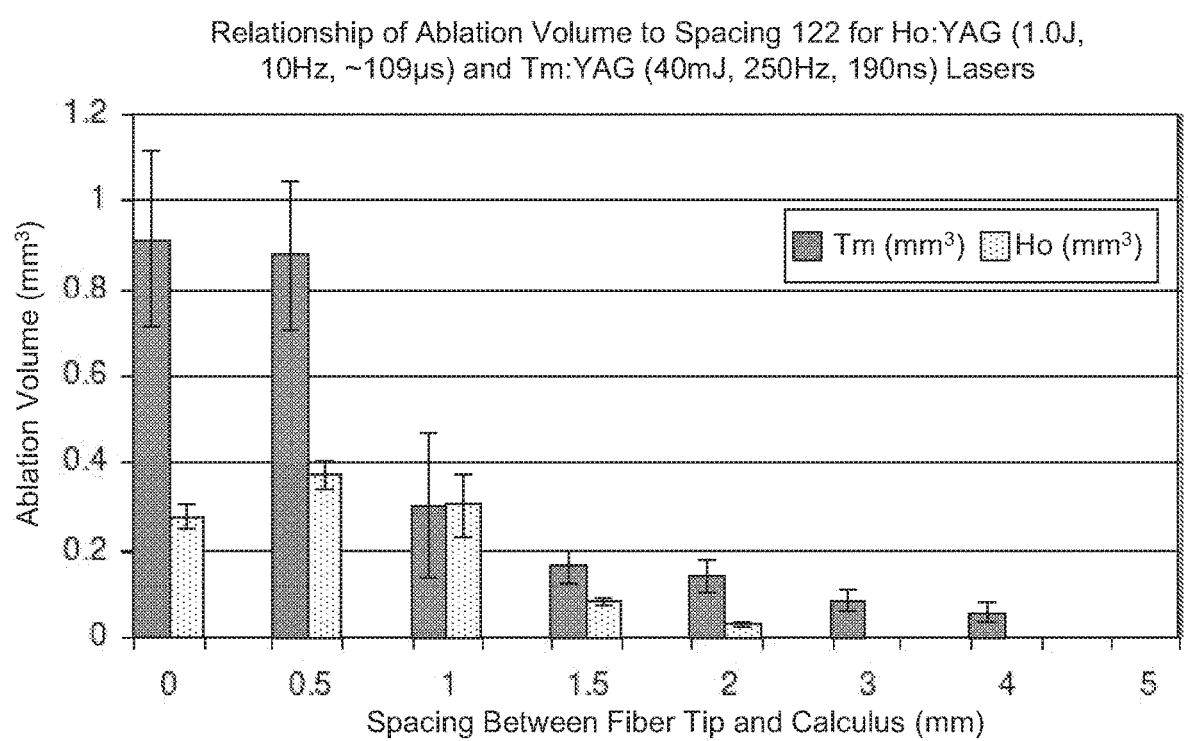
FIG. 9 is a chart illustrating a relationship between an ablation volume and a spacing between a terminating end surface or fiber tip of an optical fiber and a calculus for two exemplary lasers.

In some embodiments, the predetermined distance or spacing 122 is generally set to alleviate/control damage to the distal end 118 of the optical fiber 112, manipulate (focus or diffuse) a shock wave generated during laser lithotripsy, and improve ablation efficiency. FIG. 8 shows photos of laser lithotripsy operations using a Ho:YAG laser, and a Tm:YAG laser that show a bubble formation process and oscillations during the laser-stone interaction. FIG. 9 is a chart illustrating a relationship between an ablation volume and the spacing 122 between the terminating end surface 116 or fiber tip of the optical fiber 112 and the calculus 124 for a Ho:YAG laser (1.0 J, 10 Hz, ~109 µs) and a Tm:YAG laser (40 mJ, 250 Hz, 190 ns). The chart illustrates that the ablation efficiency for the Ho:YAG laser is higher when the spacing 122 is 0.5 mm as compared to when the surface 116 of the optical fiber 112 is in contact with the calculus 124. Additionally, the chart shows that the ablation efficiency of the Tm:YAG laser is similar over the spacing 122 of 0-0.5 mm. Thus, the spacing 122 between the surface 116 of the optical fiber 112 and the targeted object (e.g., calculus 124) provided by the fiber tip 114 can allow for efficient ablation of the targeted object while protecting the optical fiber 122. In some embodiments, the distance 122 is approximately 0.1-4 mm. In some embodiments, the distance 122 is 0.1 mm-1 mm.

In some embodiments, the fiber tip 114 is attached to the laser fiber 112, as shown in FIGS. 2 and 5-7. In some embodiments, this involves attaching the fiber tip 114 to a core of the optical fiber 112, cladding of the optical fiber 112, and/or a jacket surrounding the cladding and core of the optical fiber 112, which are not shown in order to simplify the illustrations. In some embodiments, the fiber tip 114 is removably attached to the optical fiber 112. In some embodiments, the fiber tip 114 may be attached to the distal end 118 of the optical fiber 112 by hand, and may also be detached from the optical fiber 112 by hand.

Figure 3:
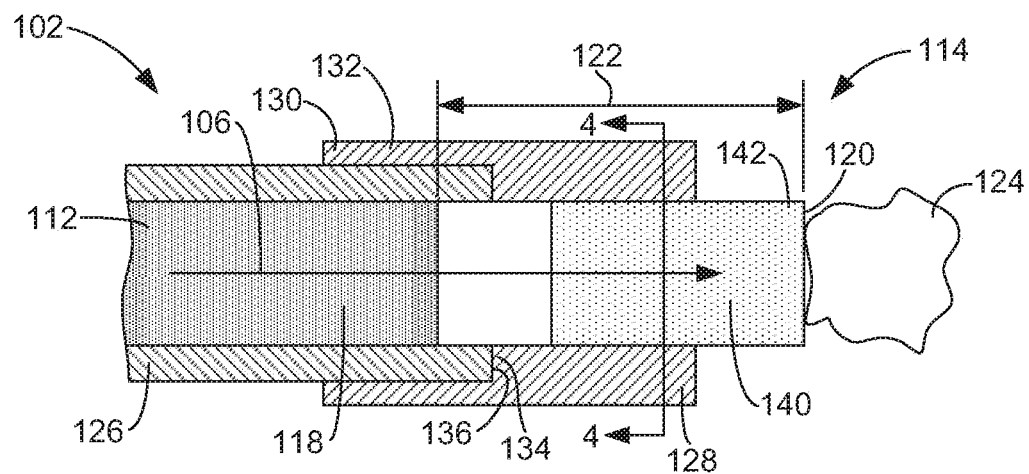
Figure 4:
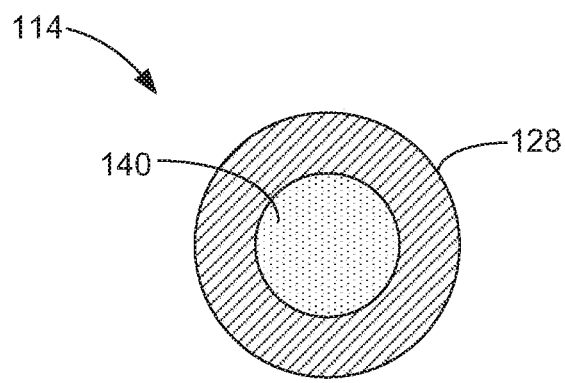
FIG. 4 is a simplified cross-sectional view of a fiber tip of FIG. 3 taken generally along line 4-4.

In some embodiments, the optical fiber 112 may be supported within a fiber support 126, as shown in FIG. 3. The fiber support 126 may be a tubular member through which the optical fiber 112 is inserted. In some embodiments, the fiber tip 114 attaches directly to the fiber support 126 rather than the optical fiber 112, as shown in FIG. 3. In some embodiments, the fiber tip 114 is removably attachable to the fiber support 126. In some embodiments, the attachment and removal of the fiber tip 114 from the fiber support 126 may be performed by hand.

In some embodiments, the fiber tip 114 includes a sleeve portion 128 that facilitates attachment of the fiber tip 114 to either the optical fiber 112 (FIG. 2) or a fiber support 126 (FIG. 3). In some embodiments, at least a proximal end 130 of the sleeve portion 128 forms a socket that is configured to receive the distal end 118 of the optical fiber 112 (FIG. 2) or a distal end 132 of the fiber support 126 (FIG. 3). In some embodiments, the sleeve portion 128 includes a shoulder 134 that is configured to engage the terminating end surface 116 of the optical fiber 112 (FIG. 2) or an end surface 136 of the fiber support 126 (FIG. 3) to position the terminating end 120 of the fiber tip 114 at the desired distance 122 from the terminating end surface 116 of the optical fiber 112.

In some embodiments, the fiber tip 114 includes a transmissive portion 140, through which the laser energy 106 discharged from the terminating end surface 116 of the optical fiber 112 is transmitted. In some embodiments, the laser energy 106 is discharged through the transmissive portion 140 along a longitudinal axis of the optical fiber 112.

Figure 5:
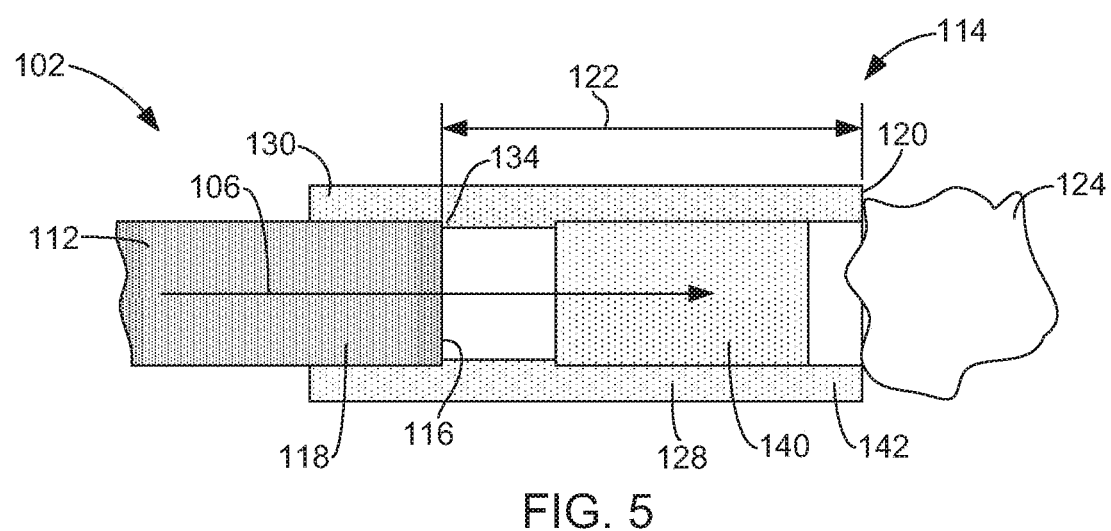
FIGS. 5-7 are simplified side cross-sectional views of a distal end of exemplary laser fibers in accordance with embodiments of the invention.

In some embodiments, the fiber tip 114 includes a spacer portion 142 that defines the distal terminating end 120 of the fiber tip 114. In some embodiments, the transmissive portion 140 includes the spacer portion 142, as shown in FIGS. 2, 3, 6 and 7. In some embodiments, the spacer portion 142 extends distally from the transmissive portion 140, as shown in FIG. 5. In some embodiments, the distal terminating end 120 of the spacer portion 142 is annular, as shown in FIG. 5. In other embodiments, the distally extending spacer portion 142 may comprise one or more projections.

In some embodiments, the sleeve portion 128 supports the transmissive portion 140 and the spacer portion 142. In some embodiments, the sleeve portion 128 surrounds the distal end 118 of the optical fiber 112. In some embodiments, the sleeve portion 128, the transmissive portion 140, and the spacer portion 142 are formed as a single component, as shown in FIG. 7.

In some embodiments, components of the fiber tip 114, such as the transmissive portion 140, the spacer portion 142, and/or the sleeve portion 128, are formed of sapphire or hard glass.

In some embodiments, the transmissive portion 140 includes one or more lenses that assist in focusing or diffusing the laser energy 106 that is directed to the targeted object, such as a calculus 124. In some embodiments, a lens 144 is located at the distal end of the transmissive portion 140, as shown in phantom in FIG. 2. In some embodiments, the transmissive portion 140 includes a lens 146 located at a proximal end of the transmissive portion 140, as shown in phantom in FIG. 2.

Figure 6:
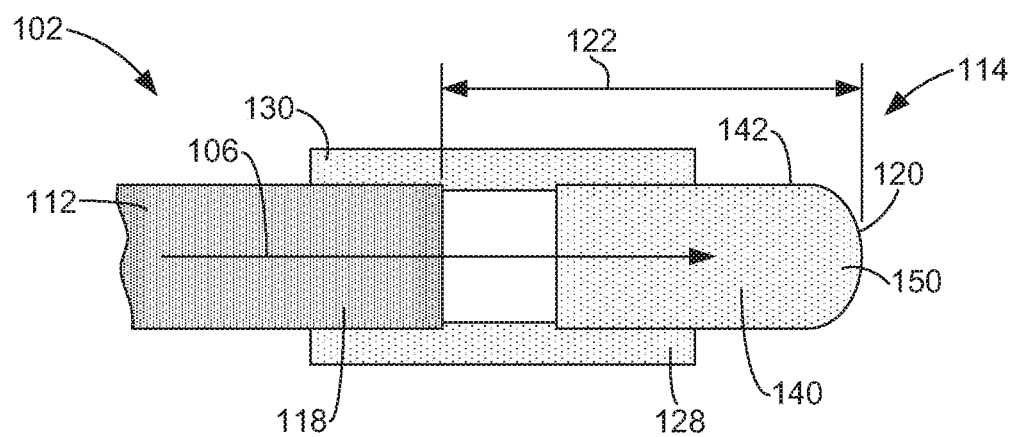
Figure 7:
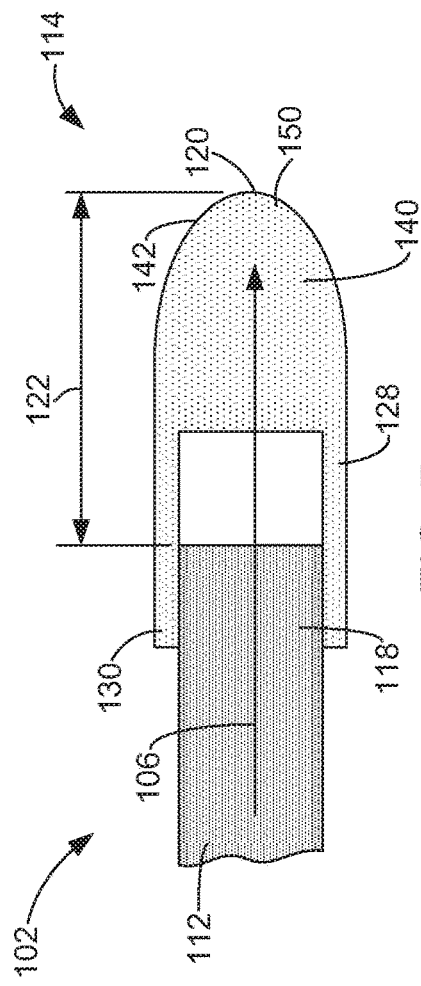

In some embodiments, the distal terminating end 120 of the fiber tip 114 includes a convex surface 150, as shown in FIGS. 6 and 7. The surface 150 may operate as the distal lens 144 (FIG. 2). In some embodiments, the convex surface 150 operates to diffuse the shock wave that occurs during laser lithotripsy to reduce retropulsion of the calculus or stone 124.

Another embodiment of the invention is directed to a method of fragmenting a calculus using a laser fiber 102 formed in accordance with one or more embodiments of the present invention. In the method, the calculus 124 is engaged with the terminating end 120 of the fiber tip 114 to position the terminating end surface 116 of the optical fiber 112 at the predetermined distance 122 from the calculus, as shown in FIGS. 2, 3 and 5. Laser energy 106 is then transmitted through the optical fiber 112 and discharged through the terminating end surface 116. The calculus or stone 124 is exposed to the laser energy 106 while the calculus is at the predetermined distance 122 from the terminating end surface 116. The calculus is then fragmented responsive to the exposure of the calculus to the laser energy 106 and the shock wave generated thereby.

Additionally, because fiber tips 114 according to the embodiments of the present invention can be detachably mounted to the laser fiber 102, the fiber tips 114 can be designed for specific procedures, types of calculi, etc. Accordingly, a single laser fiber can be used with different fiber tips 114 to perform multiple different types of procedures more efficiently and with better outcomes.

Although the present invention has been described with reference to preferred embodiments, workers skilled in the art will recognize that changes may be made in form and detail without departing from the spirit and scope of the invention.

What is claimed is:

1. A device comprising:
an optical fiber including a central longitudinal axis, a proximal end configured to receive a laser energy, and a distal end with a distal terminating end surface configured to transmit the laser energy; and
a fiber tip at the distal end of the optical fiber, the fiber tip including:
a proximal end attached to the distal end of the optical fiber;
a distal end with a distal terminating end surface; and
a transmissive body at the distal end of the fiber tip, the transmissive body being spaced apart from the distal terminating end surface of the optical fiber and comprising:
a solid interior configured to receive the laser energy from the distal terminating end surface of the optical fiber and transmit the laser energy toward the distal terminating end surface of the fiber tip;
a connector connecting the transmissive body directly to the distal end of the optical fiber, wherein the connector contacts the distal end of the optical fiber and a distalmost end of the connector is positioned between a proximalmost end of the transmissive body and a distalmost end of the transmissive body in a direction along the central longitudinal axis of the optical fiber;
wherein the connector includes a sleeve surrounding at least a portion of the transmissive body and at least a portion of the distal end of the optical fiber, and the sleeve includes a proximal facing shoulder engaging a distalmost portion of the optical fiber, wherein the shoulder connects a first radially-inward facing surface, relative to the central longitudinal axis, of the sleeve to a second radially-inward facing surface of the sleeve, and wherein the first radially-inward facing surface is spaced from the second radially-inward facing surface of the sleeve.

2. The device according to claim 1, wherein the distal terminating end surface of the fiber tip is spaced a distance from the distal terminating end surface of the optical fiber.

3. The device according to claim 2, wherein the distance is between 0.10 mm and 4 mm.

4. The device according to claim 1, wherein the optical fiber is contained within a fiber support, and the fiber tip is attached to the fiber support.

5. The device according to claim 1, wherein
the device further comprises:
a first lens attached to a proximal end of the transmissive body and disposed entirely within the sleeve; and
a second lens attached to a distal end of the transmissive body and disposed entirely outside the sleeve, wherein
a sealed cavity is disposed entirely between the first lens and the distalmost portion of the optical fiber, and a portion of the transmissive body is provided outside the sleeve.

6. The device according to claim 1, further including a lens configured to focus the laser energy transmitted from the distal terminating end surface of the optical fiber.

7. The device according to claim 1, wherein a lens portion is positioned at a proximal end of the transmissive body.

8. The device according to claim 1, wherein the proximal end of the optical fiber is configured to be optically connected to a laser generator and receive the laser energy from the laser generator.

9. The device according to claim 1, further including:
a sealed interior cavity between the distal terminating end surface of the optical fiber and a proximal end of the transmissive body, wherein
the shoulder is configured to maintain a distance between the transmissive body and the optical fiber.

10. The device according to claim 5, wherein a material of the transmissive body is different from a material of the first lens and a material of the second lens.

11. The device according to claim 10, wherein the second lens and a portion of the transmissive body extend distally of a distalmost end of the connector.

12. The device according to claim 11, wherein a distance from a radially outermost surface of the connector to the central longitudinal axis is greater than a distance from a radially outermost surface of the optical fiber to the central longitudinal axis.

13. The device according to claim 1, wherein the proximal end of the optical fiber is configured to receive a laser energy for performing laser lithotripsy,
wherein the connector creates a space between the optical fiber and the fiber tip; and
wherein the distal terminating end surface of the fiber tip is spaced a distance of 0.1 to 4 mm from the distal terminating end surface of the optical fiber so that the laser energy generates a shock wave at the distal terminating end of the fiber tip for calculus destruction.

14. The device according to claim 10, wherein the proximal end of the optical fiber is configured to receive a laser energy for performing laser lithotripsy,
wherein the connector creates a space between the optical fiber and the fiber tip;
wherein the distal terminating end surface of the fiber tip is spaced a distance of 0.1 to 4 mm from the distal terminating end surface of the optical fiber so that the laser energy generates a shock wave at the distal terminating end of the fiber tip for calculus destruction;
wherein the first lens is coupled to a proximalmost end of the transmissive body; and
wherein the second lens is coupled to a distalmost end of the transmissive body.

15. A device comprising:
an optical fiber including a proximal end configured to receive a laser energy, and a distal end with a distal terminating end surface configured to transmit the laser energy; and
a fiber tip at the distal end of the optical fiber, the fiber tip including:
a proximal end attached to the distal end of the optical fiber;
a distal end with a distal terminating end surface; and
a transmissive body spaced apart from the distal terminating end surface of the optical fiber and comprising: a solid interior configured to receive the laser energy from the distal terminating end surface of the optical fiber and transmit the laser energy toward the distal terminating end surface of the fiber tip;
a connector directly coupled to the distal end of the optical fiber and directly coupled to the transmissive body;
a first lens directly coupled to a proximalmost end of the transmissive body and directly coupled to the connector; and
a second lens directly coupled to a distalmost end of the transmissive body, wherein the second lens is positioned entirely distal from the connector and spaced from the connector and the first lens;
wherein a material of the transmissive body is different from a material of the first lens and a material of the second lens.

16. The device according to claim 15, wherein the transmissive body extends distally of a distalmost end of the connector.

17. The device according to claim 15, further including:
a sealed interior cavity between the distal terminating end surface of the optical fiber and a proximalmost end of the first lens, wherein the walls of the interior cavity consist of portions of the connector, portions of the optical fiber, and portions of the first lens.

18. A device comprising:
an optical fiber including a proximal end configured to receive a laser energy, and a distal end with a distal terminating end surface configured to transmit the laser energy; and
a fiber tip at the distal end of the optical fiber, the fiber tip including:
a proximal end attached to the distal end of the optical fiber;
a distal end with a distal terminating end surface; and
a transmissive body spaced apart from the distal terminating end surface of the optical fiber and comprising: a solid interior configured to receive the laser energy from the distal terminating end surface of the optical fiber and transmit the laser energy toward the distal terminating end surface of the fiber tip; and
a unitary sleeve that contacts both the transmissive body and the optical fiber, wherein the unitary sleeve connects the transmissive body to the optical fiber;
wherein the unitary sleeve includes a shoulder that is configured to engage the terminating end surface of the optical fiber, wherein the shoulder includes a proximally-facing surface substantially perpendicular to a central longitudinal axis of the optical fiber.

19. The device according to claim 18, wherein
the device further comprises:
a first lens attached to a proximal end of the transmissive body and disposed entirely within the sleeve; and
a second lens attached to a distal end of the transmissive body and disposed entirely outside the sleeve, wherein
a sealed cavity is disposed entirely between the first lens and the distalmost portion of the optical fiber, and
at least a portion of the transmissive body is provided outside the sleeve.

20. The device according to claim 18, further including:
a sealed interior cavity between the distal terminating end surface of the optical fiber and a proximal end of the transmissive body.

* * * * *